United States Patent [19]

Matsuba et al.

[11] Patent Number: 4,940,802
[45] Date of Patent: Jul. 10, 1990

[54] 4,4'-BIS(PHTHALIMIDO)DIPHENYL SULFONE COMPOUNDS, PROCESSES FOR THEIR PRODUCTION AND FLAME RETARDANT POLYMER COMPOSITIONS CONTAINING THEM

[75] Inventors: Takao Matsuba, Shin-nanyo; Masashige Kubo, Tokuyama; Takumi Kagawa, Shin-nanyo; Kiyotaka Oyama, Hikari; Koji Kawabata, Shin-nanyo, all of Japan

[73] Assignee: Tosoh Corporation, Shin-nanyo, Japan

[21] Appl. No.: 281,045

[22] Filed: Dec. 8, 1988

[30] Foreign Application Priority Data

Dec. 8, 1987 [JP] Japan .................. 62-308768
Dec. 8, 1987 [JP] Japan .................. 62-308771
Jul. 27, 1988 [JP] Japan .................. 63-185387

[51] Int. Cl.$^5$ .......................................... C07D 209/48
[52] U.S. Cl. ............................... 548/462; 548/476; 524/94; 524/171; 524/461; 524/89
[58] Field of Search ............... 548/462, 476, 462; 524/171, 94, 461, 89

[56] References Cited

U.S. PATENT DOCUMENTS

| 3,917,642 | 11/1975 | Wolford et al. | 548/435 |
| 4,581,396 | 4/1986 | Sonnenburg | 524/87 |
| 4,644,066 | 2/1987 | Sonnenberg | 548/462 |
| 4,769,444 | 9/1988 | Joswig et al. | 524/94 |

FOREIGN PATENT DOCUMENTS 0023402 2/1981 European Pat. Off. ............ 548/462

Primary Examiner—Anton H. Sutto
Assistant Examiner—D. D. Carr
Attorney, Agent, or Firm—Oblon, Spivak, McClelland, Maier & Neustadt

[57] ABSTRACT

A 4,4'-bis(phthalimido)diphenyl sulfone compound having the formula:

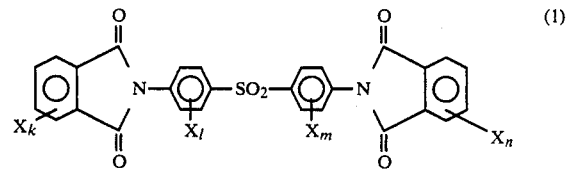

wherein X is a halogen atom, $k=0$ to 4, $l=0$ to 4, $m=0$ to 4 and $n=0$ to 4, provided $k+l+m+n>1$.

10 Claims, No Drawings

4,4'-BIS(PHTHALIMIDO)DIPHENYL SULFONE COMPOUNDS, PROCESSES FOR THEIR PRODUCTION AND FLAME RETARDANT POLYMER COMPOSITIONS CONTAINING THEM

The present invention provides novel 4,4'-bis(phthalimido)diphenyl sulfone compounds, processes for their production and flame retardant polymer compositions containing them.

Heretofore, various halogen-containing flame retardants, phosphorus-containing flame retardants, phosphorus and halogen-containing flame retardants, inorganic compounds, etc. have been known as flame retardants for synthetic polymers. However, these flame retardants in general have some difficulties in the weather resistance or heat resistance in many cases. Further, when incorporated to polymers, they are likely to bring about a deterioration of the properties of the polymers, such as a deterioration of the mechanical or electrical properties of the polymers, or coloring of the polymers. Furthermore, they have a drawback that during the molding of the polymers, the molding tank is likely to be corroded by the thermal decomposition of flame retardants.

In recent years, highly heat resistant polymers have been developed. Accordingly, the temperature at which the polymers are used, tends to be high. In order to impart flame retardancy to such highly heat resistant polymers, it is necessary to use a flame retardant thermally stable at the temperature at which such polymers are used. Further, a flame retardant is required to have good light resistance especially when the polymers containing such a flame retardant are to be used outdoors.

Therefore, it is an object of the present invention to provide a compound useful as a flame retardant having particularly high heat resistance and light resistance, and a polymer composition containing such a flame retardant.

Under these circumstances, the present inventors have synthesized various compounds and have conducted extensive researches for novel compounds capable of being suitably used as flame retardants having high heat resistance and light resistance. As a result, they have found that certain halogen-containing compounds satisfy such conditions. The present invention has been accomplished on the basis of this discovery.

The present invention provides a 4,4'-bis(phthalimido)diphenyl sulfone compound having the formula:

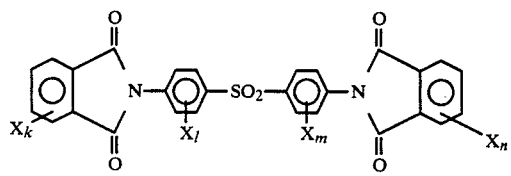

wherein X is a halogen atom, k=0 to 4, l=0 to 4, m=0 to 4 and n=0 to 4, provided k+l+m+n>1.

The present invention also provides a process for producing a 4,4'-bis(phthalimido)-diphenyl sulfone compound, which comprises reacting a phthalic anhydride compound of the formula:

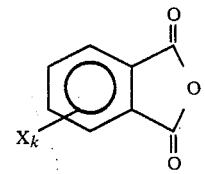

wherein X is a halogen atom, and k=0 to 4, with a 4,4'-diaminodiphenyl sulfone compound of the formula:

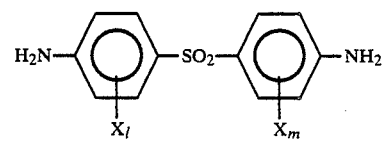

wherein X is a halogen atom, l=0 to 4, and m=0 to 4.

Further, the present invention provides another process for producing a 4,4'-bis(phthalimido)-diphenyl sulfone compound, which comprises reacting phthalic anhydride with 4,4'-diaminodiphenyl sulfone to obtain 4,4'-bis(phthalimido)diphenyl sulfone, and halogenating the 4,4'-bis(phthalimido)diphenyl sulfone.

Furthermore, the present invention provides a flame retardant polymer composition which comprises a polymer and a 4,4'-bis(phthalimido)diphenyl sulfone compound of the formula (1).

Now, the present invention will be described in detail with reference to the preferred embodiments.

The 4,4'-bis(phthalimido)diphenyl sulfone compound of the formula (1) of the present invention is a novel compound, which has at least one halogen atom in its molecule. The halogen is preferably bromine or chlorine.

Sepecific examples of the compound of the formula (1) of the present invention include 4,4'-bis(dibromophthalimido)diphenyl sulfone, 4,4'-bis(tribromophthalimido)diphenyl sulfone, 4,4'-bis(tetrabromophthalimido)diphenyl sulfone, 4,4'-bis(dibromophthalimido)-2,2'-dibromodiphenyl sulfone, 4,4'-bis(dibromophthalimido)-2,2',6,6'-tetrabromodiphenyl sulfone, 4,4'-bis(tetrabromophthalimido)-2,2',6,6'-tetrabromodiphenyl sulfone, 4,4'-bis(dichlorophthalimido)-2,2'-dibromodiphenyl sulfone, 4,4'-bis(dichlorophthalimido)-2,2',6,6'-tetrabromodiphenyl sulfone, 4,4'-bis(tetrachlorophthalimido)-2,2',6,6'-tetrabromodiphenylsulfone, 4,4'-bis(dibromophthalimido)-2,2'-dichlorodiphenyl sulfone, 4,4'-bis(dibromophthalimido)-2,2',6,6'-tetrachlorodiphenyl sulfone, 4,4'-bis(tetrabromophthalimido)-2,2',6,6'-tetrachlorodiphenyl sulfone, 4,4'-bis(dichlorophthalimido)-2,2'-dichlorodiphenyl sulfone, 4,4'-bis(dichlorophthalimido)-2,2',6,6'-tetrachlorodiphenyl sulfone, 4,4'-bis(tetrachlorophthalimido)-2,2',6,6'-tetrachlorodiphenyl sulfone, 4,4'-bis(dichlorophthalimido)diphenyl sulfone, 4,4'-bis(trichlorophthalimido)diphenyl sulfone and 4,4'-bis(tetrachlorophthalimido)diphenyl sulfone.

Now, the processes for the production of 4,4'-bis(phthalimido)diphenyl sulfone compounds of the present invention will be described in detail. For the production, there are two processes i.e. a process of reacting a phthalic anhydride compound with a 4,4'-diaminodiphenyl sulfone compound, and a process of reacting phthalic anhydride with 4,4'-diaminodiphenyl sulfone, followed by halogenation.

In the first process of reacting a phthalic anhydride compound with a 4,4'-diaminodiphenyl sulfone compound, a phthalic anhydride compound of the formula:

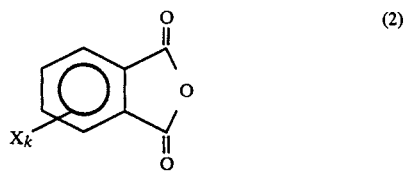
(2)

wherein X is a halogen atom, and k=0 to 4, such as phthalic anhydride, 2-bromophthalic anhydride, 3-bromophthalic anhydride, 2,3-dibromophthalic anhydride, 2,4-dibromophthalic anhydride, 2,5-dibromophthalic anhydride, 2,4-dibromophthalic anhydride, 2,3,4-tribromophthalic anhydride, 2,3,5-tribromophthalic anhydride, 2,3,4,5-tetrabromophthalic anhydride, 2-chlorophthalic anhydride, 3-chlorophthalic anhydride, 2,3-dichlorophthalic anhydride, 2,4-dichlorophthalic anhydride, 2,5-dichlorophthalic anhydride, 3,4-dichlorophthalic anhydride, 2,3,4-trichlorophthalic anhydride, 2,3,5-trichlorophthalic anhydride or 2,3,4,5-tetrachlorophthalic anhydride, is reacted with a 4,4'-diaminodiphenyl-sulfone compound of the formula:

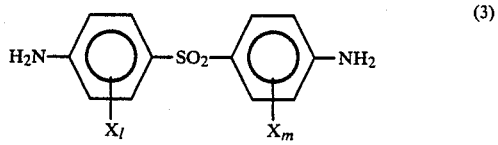
(3)

wherein X is a halogen atom, l=0 to 4, and m=0 to 4, such as 4,4'-diaminodiphenyl sulfone, 3,5,3',5'-tetrabromo-4,4'-diaminodiphenyl sulfone, 2,3,5,6,2',3',5',6'-octabromo-4,4'-diaminodiphenyl sulfone, 3,5,3',5'-tetrachloro-4,4'-diaminodiphenyl sulfone or 2,3,5,6,2',3',5',6'-octachloro-4,4'-diaminodiphenyl sulfone, to obtain a compound of the formula:

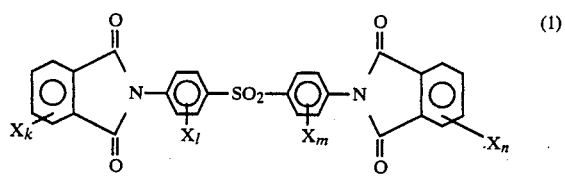
(1)

wherein X is a halogen atom, k=0 to 4, l=0 to 4, m=0 to 4, and n=0 to 4, provided k+l+m+n>1.

The proportion of the phthalic anhydride compound for the reaction is at least 2 mol times, preferably from 2 to 2.5 mol times, relative to the 4,4'-diaminodiphenyl sulfone compound.

The reaction is conducted preferably in a solvent. Benzene-type solvents such as benzene, toluene, xylene and ethyl benzene, which are at least capable of forming azeotropic mixtures with water, may be used alone or in combination as a mixture. In addition to these solvents, other solvents such as dimethylacetamide, dimethylformamide and dimethylsulfoxide, may be incorporated.

The reaction temperature may be at any level so long as water formed by the reaction can be removed as a water-solvent azeotropic mixture. The reaction is usually conducted at a temperature of from 50° to 200° C., preferably from 80° to 160° C. The reaction time is also suitably selected depending upon other conditions, and there is no particular restriction as to the reaction time. However, the reaction time is usually at least 30 minutes, preferably at least one hour.

The second process comprises reacting phthalic anhydride with 4,4'-diaminodiphenyl sulfone, and halogenating the resulting 4,4'-bis(phthalimido)diphenylsulfone.

Phthalic anhydride is used in an amount of at least 2 mol times, preferably from 2 to 2.5 mol times, relative to 4,4'-diaminodiphenyl sulfone. The reaction is conducted in a benzene-type solvent capable of at least forming an azeotropic mixture with water.

The reaction temperature may be at any level so long as water formed by the reaction can be removed as a water-solvent azeotropic mixture. The reaction is usually conducted at a temperature of from 50° to 200° C., preferably from 80° to 160°. The reaction time is suitably selected depending upon other conditions, and there is no particular restriction as to the reaction time. However, it is usually at least 30 minutes, preferably at least one hour.

Then, 4,4'-bis(phthalimido)diphenyl sulfone is halogenated.

The halogenation is conducted by means of a halogenating agent such as $Br_2$, $Cl_2$ or BrCl in a reaction solvent such as $Br_2$—$CH_2Cl_2$ or $SO_3$—$H_2SO_4$ in the presence of a halogenation catalyst such as $SbCl_5$ or Fe. The halogenating agent is used in an amount of at most 50 mol times relative to 4,4'-bis(phthalimido)diphenyl sulfone. The reaction is conducted at a temperature of from −50° to 100° C., preferably from −20° to 50° C. for from 1 to 20 hours.

The novel 4,4'-bis(phthalimido)diphenyl sulfone compounds of the present invention are useful as flame retardants for polymers having high melting points and excellent weather resistance and heat resistance. Now, the flame retardant polymer composition of the present invention will be described in detail.

In the present invention, the polymer to which the novel compound of the formula (1) is incorporated as a flame retardant, is not particularly limited and includes thermoplastic resins or elastomers such as a polyethylene, a polypropylene, a polybutene, an ethylene-vinyl acetate copolymer, an ethylen-ethyl acrylate copolymer, an ethylene-propylene copolymer, an ethylene-propylene-diene copolymer, an ethylene-vinyl chloride copolymer, an ethylene-vinyl acetate-graft vinyl chloride copolymer, an ethylene-ethyl acrylate-graft vinyl chloride copolymer, an ethylene-propylene-graft vinyl chloride copolymer, a chlorinated polyethylene, a chlorinated polyethylene-graft vinyl chloride copolymer, a polyamide, an acrylic resin, a polystyrene, a polycarbonate, a polybutyleneterephthalate and an acrylonitrile-butadiene-styrene copolymer, thermosetting resins such as a polyester, a polyurethane, an epoxy resin, a phenol resin, a melanine resin and a urea resin, and a butyl rubber, a chloroprene rubber, a nitrile rubber, a natural rubber, a silicon rubber, a chlorosulfonated polyethylene, a styrene-butadiene rubber, a styrene-butadiene-acrylonitrile copolymer, and a polyester-ether elastomer. These polymers may be used alone or in combination as a mixture of two or more.

The amount of the compound of the formula (1) to be used as a flame retardant for a synthetic polymer, may be optionally selected, but is usually within a range of from 3 to 100 parts by weight, preferably from 10 to 50 parts by weight relative to 100 parts by weight of the synthetic polymer. If the amount is less then 3 parts by weight, the effects for flame retardancy will be inadequate. If the amount exceeds 100 parts by weight, no additional effects will be obtained.

When the compound of the formula (1) is to be used as a flame retardant for a synthetic polymer, the manner of the addition to the polymer may be optionally selected and is not particularly limited. For example, there may be mentioned a method in which the polymer and the flame retardant are mixed in the form of chips or powders, a method wherein such a mixture is melted and molded, a method wherein the flame retardant is added at the end of the polymerization of the polymer, or a method wherein the polymer and the flame retardant are formed into the respective solutions, which are then mixed and subjected to reprecipitation with a poor solvent, followed by evaporation of the solvent.

Further, when the compound of the formula (1) is used as a flame retardant for a synthetic polymer, a flame retardant assistant (such as antimony trioxide) or other known flame retardants may be incorporated for the purpose of increasing the flame retardancy. Further, other known additives (such as a stabilizer, a coloring agent, an ultraviolet absorber, etc.) may also be incorporated.

The polymer composition in which the novel compound of the present invention is incorporated, is free from evaporation or dissipation of the flame retardant and is particularly excellent in the light resistance and heat resistance. Further, as shown in Table 3, it is superior in the whiteness to conventional imide compounds.

Now, the present invention will be described in further detail with reference to Examples. However, it should be understood that the present invention is by no means restricted to such specific Examples.

EXAMPLE 1

Into a 3l four-necked flat bottom separable flask provided with a cooling condenser equipped with a calcium chloride tube, a water separator and a power stirrer, 268.9 g (577.9 mmol) of tetrabromophthalic anhydride, 71.8 g (289.0 mmol) of 4,4'-diaminodiphenyl sulfone, 1,100 ml of dimethylacetamide and 500 ml of ethylbenzene were sequentially added. Then, the mixture was heated to 80° C. under stirring on an oil bath to obtain a uniform solution. The solution was heated to 136° C. over a period of one hour, and water formed in the system was removed under an azeotropic condition of ethylbenzene-water. As water was distilled off, crystals precipitated. Four hours later, the distillation of water was completed, the stirring was stopped, and the mixture was cooled to room temperature. The precipitated crystals were collected by filtration, washed sequentially with 200 ml of dimethylacetamide and with 500 ml of isopropyl alcohol and then dried (at 200° C. for two hours) to obtain slightly yellow crystals. The melting point of the crystals was at least 300° C. The IR spectrum of the substance thus obtained was measured, whereby formation of a phthalimide structure was confirmed by disappearance of the stretching vibration of $C=O$ of the acid anhydride at 1,760 cm$^{-1}$ and formation of new stretching vibration of $C=O$ of a phthalimide at 1,712 cm$^{-1}$. Further, stretching vibration of $O=S=O$ was observed at 1,340 cm$^{-1}$, and anti-symmetric stretching vibration of $O=S=O$ was observed at 1,120 cm$^{-1}$. Further, the values of the elemental analysis were C:29.6%, H:0.8%, Br:56.3% and N:2.5%, which agreed to the calculated values (C:29.51%, H:0.71%, Br:56.09% and N:2.46%). Further, the product was confirmed to be pure by the analysis by high performance gel permeation liquid chromatography by means of a column of TSK GEL G-1,000H (manufactured by TOSOH CORPORATION) (eluent: tetrahydrofuran). From the foregoing data, it was confirmed that a compound of the formula (1) wherein X is Br, k=n=4 and l=m=0, was produced.

The thermal stability of the compound thus obtained was analyzed under the following conditions by TGA. The results are shown in Table 1.

Gas: Air,
Gas Flow: 30.50 ml/min,
Rate: 10° C./min,
Hold: 30 min,
Temp.: room temp. to 500° C.

TABLE 1

| TG loss (wt %) | °C. | TG loss (wt %) | °C. |
|---|---|---|---|
| Initiation | 383 | 20 | 435 |
| 5 | 412 | 40 | 453 |
| 10 | 422 | 50 | 473 |
| Melting point | | 365–367° C. | |
| | | (DTA max 366° C.) | |

As shown above, the compound obtained had very high heat resistance.

EXAMPLE 2

Into a 200 ml four-necked flask provided with a cooling condensor equipped with a calcium chloride tube, a water seperator and a power stirrer, 9.30 g (37.5 mmol) of 4,4'-diaminodiphenyl sulfone, 11.1 g (74.9 mmol) of phthalic anhydride, 20 ml of ethylbenzene and 20 ml of dimethylacetamide were sequentially added. Then, the mixture was heated to 80° C. under stirring on an oil bath to obtain a uniform solution. The solution was heated to 150° C. over a period of one hour, and water formed in the system was removed under an azeotropic condition of ethylbenzene-water. Four hours later, the distillation of water was completed, and 100 ml of ethylbenzene was added. The stirring was stopped, and the mixture was left to cool to the room temperature. Crystals were collected by filtration, washed sequentially with 100 ml of ethylbenzene and with 100 ml of carbon tetrachloride and dried (at 140° C. for 2 hours) to obtain slightly yellow crystals. The melting point of the crystals was at least 300° C. The IR spectrum of the substance thus obtained was measured, whereby formation of a phthalimide structure was confirmed by disappearance of the stretching vibration of $C=O$ of the acid anhydride at 1,765 cm$^{-1}$ and formation of new stretching vibration of $C=O$ of phthalimide at 1,710 cm$^{-1}$. Further, stretching vibration of $O=S=O$ was observed at 1,320 cm$^{-1}$, and anti-symmetric stretching vibration of $O=S=O$ was observed at 1,105 cm$^{-1}$. Further, the values of the elemental analysis were C:66.1%, H:3.3% and N:5.6%, which agreed to the calculated values (C:66.14%, H:3.17% and N:5.51%). The product was confirmed to be pure by the analysis by high performance gel permeation liquid chromatography by means of a column of TSK GEL G-1,000 H (manufactured by TOSOH CORPORATION) (eluent: tetrahydrofuran).

To 1.0 g of 4,4'-bis(phthalimido)diphenyl sulfone obtained above, 4.0 ml of conc-$H_2SO_4$, 8.0 ml of $SO_3$, 50 mg of Fe and 1 mg of iodine were added sequentially. Then, 3.6 ml of $Br_2$ was dropwise added thereto at 40° C. over a period of 4 hours. After stirring at 40° C. for 2 hours, the temperature was raised to 100° C. to distill off $Br_2$ and $SO_3$. After cooling the mixture to a room temperature, it was added to 200 ml of water. Formed precipitates were collected by filtration, washed with 50 ml of isopropyl alcohol and dried at 200° C. for 2 hours to obtain slightly yellow crystals. The IR spectrum of the substance thus obtained, was measured, whereby stretching vibration of C=O of a phthalimide was observed at 1,712 $cm^{-1}$, stretching vibration of O=S=O was observed at 1,340 $cm^{-1}$ and anti-asymmetric stretching vibration of O=S=O was observed at 1,120 $cm^{-1}$. Further, the values of the elemental analysis were C:29.8%, H:0.9%, Br:54.1% and N:2.5% (calculated values are C:29.51%, H:0.71%, Br:56.09% and N:2.46%), whereby it was found that 7.6 bromine atoms were introduced per one molecule of 4,4'-bis(phthalimido)diphenyl sulfone. Further, the product was confirmed to be pure by the analysis by high performance gel permeation liquid chromatography by means of a column of TSK GEL G-1,000 H (manufactured by TOSOH CORPORATION) (eluent: tetrahydrofuran). From the foregoing data, it was confirmed that a compound of the formula (1) wherein X is Br and k+l+m+n=7.6, was obtained.

The thermal stability of the compound thus obtained was analyzed under the same condition as in Example 1. The results was the same as in the case of Example 1.

EXAMPLES 3 to 6

To pellets of polypropylene (Chisso K7014, Impact resistant grade), the compound in the amount as identified in Table 2 (parts by weight) was kneaded by rolls at 180° C. for 12 minutes. The roll kneadability was evaluated to be "good" only when no resin or flame retardant adhered to the rolls and no decomposition of the flame retardant was observed. The kneaded composition was heat-pressed (100 kg/$cm^2$) at 200° C. for two minutes and cooled for five minutes at 30° C. under pressure (100 kg/$cm^2$) to obtain a sheet having a thickness of 3 mm. A test piece for the measurement of oxygen index (OI) was prepared from this sheet in accordance with JIS K-7201-1972, and OI was measured. The results are shown in Table 2. Further, to the press-molded sheet, ultraviolet rays (290–450 nm, ultraviolet intensity: 100 mW/$cm^2$) were irradiated at 63° C. for 50 hours, and the ΔE values (color differences) before and after the irradiation are shown also in Table 2.

COMPARATIVE EXAMPLE 1

Pellets of polypropylene (Chisso K7014, Impact resistant grade) were melted alone on rolls at 180° C. for 12 minutes, heat-pressed (100 kg/$cm^{-2}$) at 200° C. for two minutes and cooled for 5 minutes at 30° C. under pressure (100 kg/$cm^{-2}$) to obtain a polypropylene sheet having a thickness of 3 mm. The evaluation was made in the same manner as in Example 1. The results are shown in Table 2.

COMPARATIVE EXAMPLES 2 AND 3

To pellets of polypropylene (Chisso K7014, Impact resistant grade), the compound in the amount as identified in Table 2 was kneaded by rolls at 180° C. for 12 minutes. The kneaded composition was heat-pressed (100 kg/$cm^{-2}$) at 200° C. for two minutes and cooled for 5 minutes at 30° C. under pressure (100 kg/$cm^{-2}$) to obtain a sheet having a thickness of 3 mm. The evaluation was made in the same manner as in Example 1. The results are shown in Table 2.

TABLE 2

| | Comparative Example 1 | Comparative Example 2 | Comparative Example 3 | Example 3 | Example 4 | Example 5 | Example 6 |
|---|---|---|---|---|---|---|---|
| Polypropylene (Chisso K7014) | 100 | 100 | 100 | 100 | 100 | 100 | 100 |
| DBDE *1 | — | 30 | 40 | — | — | — | — |
| Compound (1) *2 of the present invention | — | — | — | 30 | 40 | — | — |
| Compound (2) *3 of the present invention | — | — | — | — | — | 30 | 40 |
| $Sb_2O_3$ | — | 10 | 13.3 | 10 | 13.3 | 10 | 13.3 |
| Roll kneadability | Good | Good | Good | Good | Good | Good | Good |
| OI | 17.5 | 22.4 | 23.2 | 23.2 | 24.1 | 23.2 | 24.1 |
| ΔE | 8.9 | 17.6 | 20.1 | 4.3 | 3.7 | 4.3 | 3.9 |

EXAMPLE 7

Into a 3l four-necked flat bottom separable flask provided with a cooling condenser equipped with a calcium chloride tube, a water separator and a power stirrer, 268.9 g (577.9 mmol) of tetrabromophthalic anhydride, 1.8 g (289.0 mmol) of 4,4'-diaminodiphenyl sulfone, 1,100 ml of dimethylacetamide and 500 ml of ethylbenzene were sequentially added. Then, the mixture was heated to 80° C. under stirring on an oil bath to obtain a uniform solution. The solution was heated to 136° C. over a period of one hour, and water formed in the system was removed under an azeotropic condition of ethylbenzene-water. As water was distilled off, crystals precipitated. Four hours later, the distillation of water was completed, the stirring was stopped, and the mixture was cooled to room temperature. The precipitated crystals were collected by filtration, washed sequentially with 200 ml of dimethylacetamide and with 500 ml of isopropyl alcohol and then dried (at 200° C. for two hours) to obtain slightly yellow crystals. The melting point of the crystals was at least 300° C. The IR spectrum of the substance thus obtained was measured, whereby formation of a phthalimide structure was comfirmed by disappearance of the stretching vibration of C=O of the acid anhydride at 1,760 $cm^{-1}$ and formation of new stretching vibration of C=O of a phthalimide at 1,712 cm$^{-1}$. Further, stretching vibration of O=S=O was observed at 1,340 cm$^{-1}$, and anti-symmetric stretching vibration of O=S=O was observed at 1,120 cm$^{-1}$. Further, the values of the elemental analysis were C:29.6%, H:0.8%, Br:56.3% and N:2.5%, which agreed to the calculated values (C:29.51%, H:0.71%, Br:56.09% and N:2.46%). Further, the product was confirmed to be pure by the analysis by high performance gel permeation chromatography by means of a column of TSK GEL G-1,000 H (manufactured by TOSOH CORPORATION) (eluent: tetrahydrofuran). From the foregoing data, it was confirmed that bis(tetrabromophthalimido)diphenyl sulfone (hereinafter referred to as TBPS) of the formula (1) wherein X is Br, k=n=4 and l=m=0, was produced.

The thermal stability of the compound thus obtained was analyzed under the following conditions by TGA. The color of the crystals was measured, and the Hunter whiteness (W) and the yellow index (YI) were calculated. The results are shown in Table 3.
Gas: Air,
Gas Flow: 30.05 ml/min,
Rate: 10° C./min, Temp.: room temp. to 500° C.

COMPARATIVE EXAMPLES 4 and 5

Comparative Example 4 relates to DBDE (decabromodiphenyl ether). Comparative Example 5 relates to BT-93 (bis(tetrabromophthalimido)ethane). These compounds were evaluated in the same manner as in Example 7, and the results are shown in Table 3.

EXAMPLES 8 to 11

To a high impact resistance polystyrene resin (Idemitsu Styrol HT50, hereinafter referred to as HIPS), other components were blended to obtain a mixture having the composition (parts by weight) as identified in Table 4-1. The mixture was pelletized by extrusion at an extruding temperature of 220° C. by means of D20-25 extruder of Laboplastomill manufactured by Toyo Seiki Seisakusho. Pellets were heat-pressed (100 kg/cm$^2$) at 230° C. for 5 minutes and cooled for five minutes at 30° C. under pressure (100 kg/cm$^2$) to obtain a sheet having a thickness of 3 mm. A test piece for the measurement of oxygen index (OI) was prepared from this sheet in accordance with JIS K-7001-1972, and OI was measured. A test piece having a thickness of 3 mm for the measurement of UL94 flammability was prepared, and the vertical flame test was conducted. As regards bleed out, a molded sheet was left to stand for 30 days, and the surface condition was evaluated visually. The results are shown in Table 4-1. Further, press-molded sheets having a thickness of 3 mm were left to stand at 120° C. for 50 hours and 100 hours, respectively, and the ΔE values (color differences) after being left were measured to evaluate the heat resistance. Further, to press-molded sheets having a thickness of 3 mm, ultraviolet rays (290-450 nm, ultraviolet intensity: 100 m W/cm$^2$) were irradiated at 63° C. for 5 hours and 10 hours, respectively, and the ΔE values (color differences) before and after the irradiation were measured to evaluate the light resistance. These results are shown in Table 5.

COMPARATIVE EXAMPLES 6 to 14

HIPS (Idemitsu Styrol HT-50) alone or the mixture having the composition as identified in Table 4-2 was pelletized by extrusion at an extruding temperature of 220° C. by means of D20-25 extruder of Laboplastmill manufactured by Toyo Seiki Seisakusho. Then, the evaluations were conducted in the same manner as in Examples 8 to 11. The results are shown in Tables 4-2 and 5.

TABLE 3

|  | TG loss temp. (°C.) | | | Hunter whiteness W[1] | Yellow Index YI[2] |
| --- | --- | --- | --- | --- | --- |
|  | 5% | 20% | 50% | | |
| Example 7 | 470 | 474 | 500 | 96.30 | 4.97 |
| Comparative Example 4 | 372 | 387 | 432 | 96.12 | 5.66 |
| Comparative Example 5 | 432 | 447 | 471 | 82.03 | 27.37 |

[1] $W = 100 - [(100-L)^2 + (a^2 + b^2)]^{\frac{1}{2}}$
[2] $YI = (1.28 X - 1.06 Z) \times 100/Y$

TABLE 4-1

|  | Example 8 | Example 9 | Example 10 | Example 11 |
| --- | --- | --- | --- | --- |
| HIPS[1] | 100 | 100 | 100 | 100 |
| DBDE[2] | — | — | — | — |
| BT-93[3] | — | — | — | — |
| TBPS[4] | 5 | 10 | 15 | 20 |
| Surfactant[5] | 0.5 | 0.5 | 0.5 | 0.5 |
| SB$_2$O$_3$ | 1.67 | 3.33 | 5.00 | 6.67 |
| OI | 20.6 | 21.9 | 24.1 | 27.2 |
| UL94 | V2 | V2 | V0 | V0 |
| Bleed out | Nil | Nil | Nil | Nil |

[1] Idemitsu Styrol HT-50
[2] Decabromodiphenyl ether
[3] Bis(tetrabromophthalimido)ethane
[4] Bis(tetrabromophthalimido)diphenyl sulfone
[5] Kao (Emulgen 912)

TABLE 4-2

|  | Example 6 | Example 7 | Example 8 | Example 9 | Example 10 | Example 11 | Example 12 | Example 13 | Example 14 |
| --- | --- | --- | --- | --- | --- | --- | --- | --- | --- |
| HIPS[1] | 100 | 100 | 100 | 100 | 100 | 100 | 100 | 100 | 100 |
| DBDE[2] | — | 5 | 10 | 15 | 20 | — | — | — | — |
| BT-93[3] | — | — | — | — | — | 5 | 10 | 15 | 20 |
| TBPS[4] | — | — | — | — | — | — | — | — | — |
| Surfactant[5] | — | 0.5 | 0.5 | 0.5 | 0.5 | 0.5 | 0.5 | 0.5 | 0.5 |
| SB$_2$O$_3$ | — | 1.67 | 3.33 | 5.00 | 6.67 | 1.67 | 3.33 | 5.00 | 6.67 |
| OI | 16.7 | 19.7 | 24.1 | 27.2 | 28.5 | 20.6 | 22.8 | 24.1 | 27.2 |
| UL94 | <V2 | V2 | V2 | V0 | V0 | V2 | V2 | V0 | V0 |
| Bleed out | Nil | Nil | Nil | Nil | Nil | Nil | Nil | Nil | Nil |

[1] Idemitsu Styrol HT-50
[2] Decabromodiphenyl ether
[3] Bis(tetrabromophthalimido)ethane
[4] Bis(tetrabromophthalimido)diphenyl sulfone
[5] Kao (Emulgen 912)

TABLE 5

|  | Example 10 | Comparative Example 6 | Comparative Example 9 | Comparative Example 13 |
| --- | --- | --- | --- | --- |
| ΔE after 5 hours of light resistance test | 18.20 | 17.91 | 53.71 | 20.80 |
| ΔE after 10 hours of light resistance test | 33.77 | 24.28 | 54.28 | 35.85 |
| ΔE after 50 hours of heat resistance test | 6.50 | 16.82 | 16.12 | 7.20 |
| ΔE after 100 hours of heat resistance test | 10.52 | 24.99 | 23.78 | 11.84 |

$\Delta E = (\Delta L^2 + \Delta a^2 + \Delta b^2)^{\frac{1}{2}}$

We claim:

1. A 4,4'-bis(phthalimido)diphenyl sulfone compound having the formula:

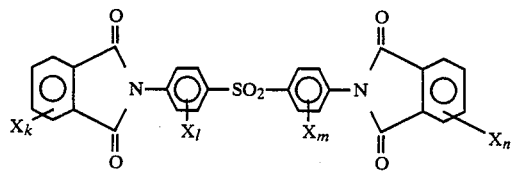
(1)

wherein X is a halogen atom, $k=0$ to 4, $l=0$ to 4, $m=0$ to 4 and $n=0$ to 4, provided $k+l+m+n>1$.

2. The compound of the formula (1) according to claim 1, wherein X is bromine or chlorine.

3. A process for producing a 4,4'-bis(phthalimido)-diphenyl sulfone compound, which comprises reacting a phthalic anhydride compound of the formula:

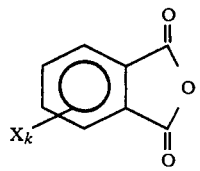
(2)

wherein X is a halogen atom, and $k=0$ to 4, with a 4,4'-diaminodiphenyl sulfone compound of the formula:

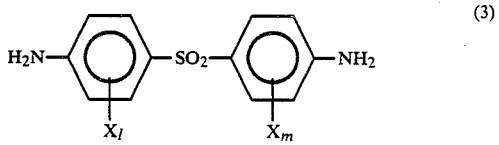
(3)

wherein X is a halogen atom, $l=0$ to 4, and $m=0$ to 4.

4. A process for producing a 4,4'-bis(phthalimido)-diphenyl sulfone compound, which comprises reacting phthalic anhydride with 4,4'-diaminodiphenyl sulfone to obtain 4,4'-bis(phthalimido)diphenyl sulfone, and halogenating the 4,4'-bis(phthalimido)diphenyl sulfone.

5. A flame retardant polymer composition which comprises a polymer and a 4,4'-bis(phthalimido)diphenyl sulfone compound of the formula (1) as defined in claim 1.

6. The flame retardant polymer composition according to claim 5, wherein X in the formula (1) is bromine or chlorine.

7. The flame retardant polymer composition according to claim 6, wherein the compound of the formula (1) is in an amount of from 3 to 100 parts by weight relative to 100 parts by weight of the polymer.

8. A compound of the formula (I) according to claim 1, bis(tetrabromophthalimido)diphenylsulfone.

9. The flame retardant polymer composition according to claim 5, wherein the compound of the formula (I) is bis(tetrabromophthalimido)diphenylsulfone.

10. The flame retardant polymer composition according to claim 9, wherein the polymer is a polystyrene or polypropylene resin.

* * * * *